(12) United States Patent
Lord et al.

(10) Patent No.: US 8,515,887 B2
(45) Date of Patent: Aug. 20, 2013

(54) DECISION SUPPORT SYSTEM WITH EMBEDDED CLINICAL GUIDELINES

(75) Inventors: William P. Lord, Fishkill, NY (US); Colleen M. Ennett, White Plains, NY (US); Xinxin Zhu, Croton-N-Hudson, NY (US); Joachim D. Schmidt, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1360 days.

(21) Appl. No.: 12/093,382

(22) PCT Filed: Nov. 6, 2006

(86) PCT No.: PCT/IB2006/054129
§ 371 (c)(1), (2), (4) Date: Sep. 29, 2008

(87) PCT Pub. No.: WO2007/054882
PCT Pub. Date: May 18, 2007

(65) Prior Publication Data
US 2009/0119282 A1     May 7, 2009

Related U.S. Application Data

(60) Provisional application No. 60/735,928, filed on Nov. 10, 2005.

(51) Int. Cl.
*G06F 17/30* (2006.01)
*G06N 5/04* (2006.01)
*G06E 1/02* (2006.01)

(52) U.S. Cl.
USPC .............................................. 706/45; 706/20

(58) Field of Classification Search
USPC ........................................................... 706/45
See application file for complete search history.

(56) References Cited

U.S. PATENT DOCUMENTS

| | | |
|---|---|---|
| 6,604,114 B1 | 8/2003 | Toong |
| 2002/0077849 A1 | 6/2002 | Baruch |
| 2003/0023534 A1 | 1/2003 | Kadambe |
| 2003/0088559 A1 | 5/2003 | Teranishi |
| 2005/0038678 A1 | 2/2005 | Qian |

FOREIGN PATENT DOCUMENTS

| | | |
|---|---|---|
| CN | 1417709 A | 5/2003 |
| EP | 0303231 A2 | 2/1989 |
| EP | 1480151 A2 | 11/2004 |
| WO | 0225528 A1 | 3/2002 |
| WO | 2005059803 A2 | 6/2005 |

(Continued)

OTHER PUBLICATIONS

Yu et al. (Yu), "HDA—An Internet-Enabled System for Healthcare Management", 2000.*

(Continued)

*Primary Examiner* — Jeffrey A Gaffin
*Assistant Examiner* — Nathan Brown, Jr.

(57) ABSTRACT

A context-aware decision-support system automatically selects the clinical guideline pertaining to the patient's medical care and automatically deduces the current stage in the guideline (S312, S336). The system tracks a patient's progress through the guideline to maintain a determination as to the current stage (S304, S336). Based on the current stage and patient-specific information, an unsolicited recommendation is presented on-screen, accompanied by one or more grades representing the level of evidence underlying the recommendation (S344).

17 Claims, 3 Drawing Sheets

FIG. 3

(56) References Cited

FOREIGN PATENT DOCUMENTS

WO 2004016218 A2 2/2004
WO 2005034001 A1 4/2005

OTHER PUBLICATIONS

Bayegan, E. et al "The Helpful Patient Record System: Problem Oriented and Knowledge Based" Norwegian Univ. of Science and Technology, Jul. 2005.

Ciccrese, Paolo et al "A Guideline Management System" Medinfo. Proceedings of the COnf. on Medical Informatics, vol. 11, No. 1 Sep. 2004, pp. 28-32.

Yu, Xudong W. et al "HDA—An Internet-Enabled System for Healthcare Management", Systems, Man, and Cybernetics, IEEE Int'l Conf., vol. 3, Oct. 8, 2000, pp. 1836-1841.

* cited by examiner

DECISION SUPPORT SYSTEM WITH EMBEDDED CLINICAL GUIDELINES

The present invention relates to automatic decision support and particularly to decision support by a system that is automatically context-aware.

One of the biggest challenges for a context-aware decision support system would be to accurately identify what clinical guideline(s) apply to the current medical care of a patient or medical subject and where the patient is in the guideline. This capability would allow the system to automatically retrieve and present pertinent information to medical personnel in a timely manner. This information includes, but is not limited to: data required to make the next decision in the patient's care, e.g., diagnostic test, treatment, extubation, discharge; standard order sets such as those issued by the physician to a laboratory for a specific workup on a specimen; reference material; identification of missed steps; identification of all steps taken so far; alerts; scheduling information, including user interface to schedule resources and staff; documentation templates; and educational material for the patient or patient's family.

Assistance in the selection of the most appropriate next step with respect to tests and procedures is valuable to guide the patient through the healthcare system as quickly, efficiently and cost-effectively as possible. Automated assistance with embedded clinical guidelines and protocols would also help to ensure that clinicians adhere to these guidelines and protocols as defined by each institution to maintain high quality of patient care. As a further benefit, all patients would receive the same care regardless of physical location or expertise of the attending physician.

Systems that require the user to identify the stage of patient care, in order to present the appropriate information for clinical decision-making, are cumbersome and time-consuming for the user. The need to manually enter the identification serves as a deterrent to use of the system.

Another barrier to general acceptance of such a system is lack of facility offered to a clinician in tracing back the evidence that would back up the specific recommendation, e.g., a proposed next step in medical care. Clinicians rarely take the time to use systems that offer links to reference articles in a real-time clinical setting, but would be more likely to look at such evidence if it were to be provided directly.

The difficulty in accessing this evidence can lead to the clinician selecting the next test or procedure based on personal preference or comfort level with the technologies involved. Also, the clinician may own equipment to run specific tests or receive remuneration from a clinic for referrals. This affects the quality of care that patients receive, as well as healthcare system costs.

To overcome the above-noted shortcomings, a decision support initialization device according to the present invention, searches through an electronic record of service for identifiers. As a result, the current stage of service in a predetermined multi-step service guideline can automatically be deduced. This allows a clinician's decision to be made based on the deduced current stage.

In another aspect, a context-aware decision support apparatus includes a module for automatically deducing a current stage of service. In addition to a user interface, the apparatus has a recommending module to be activated for automatically, and without user intervention, retrieving and presenting information to the user. The information includes a predetermined grade symbolizing level of confidence in evidence underlying a recommendation that is based on the deduced current stage. This information is presented on the user interface, along with the recommendation.

In a further aspect, a decision support initialization device includes separately-located user interfaces and a processor for searching through an electronic record of service to enable automatic deduction of a current stage of service in a predetermined multi-step guideline. The deducing is based on the search and the location of a user interface that is being operated. Thus, a decision can be made based on the deduced current stage.

Details of the novel decision support are set forth below with the aid of the following drawings, wherein.

Deviations from guidelines and protocols may lead to lower quality of care. Hospital administrators want clinicians to adhere to guidelines and protocols to ensure a high quality of care for all patients. Embedded guidelines and protocols enable better tracking and assessment of quality of care indices, which is desirable from an administrator's point of view. Reports on quality of care could attract more patients to the institution and reduce paperwork as part of the quality management program for reporting these measures to the Joint Commission on Accreditation of Healthcare Organizations (JCAHO) to retain accreditation.

Recommendations for next steps are useful for clinicians working on the edges of their area of expertise or in an emergency department (ED) setting where doctors are commonly presented with a wide range of patient types and situations.

Figure 1:
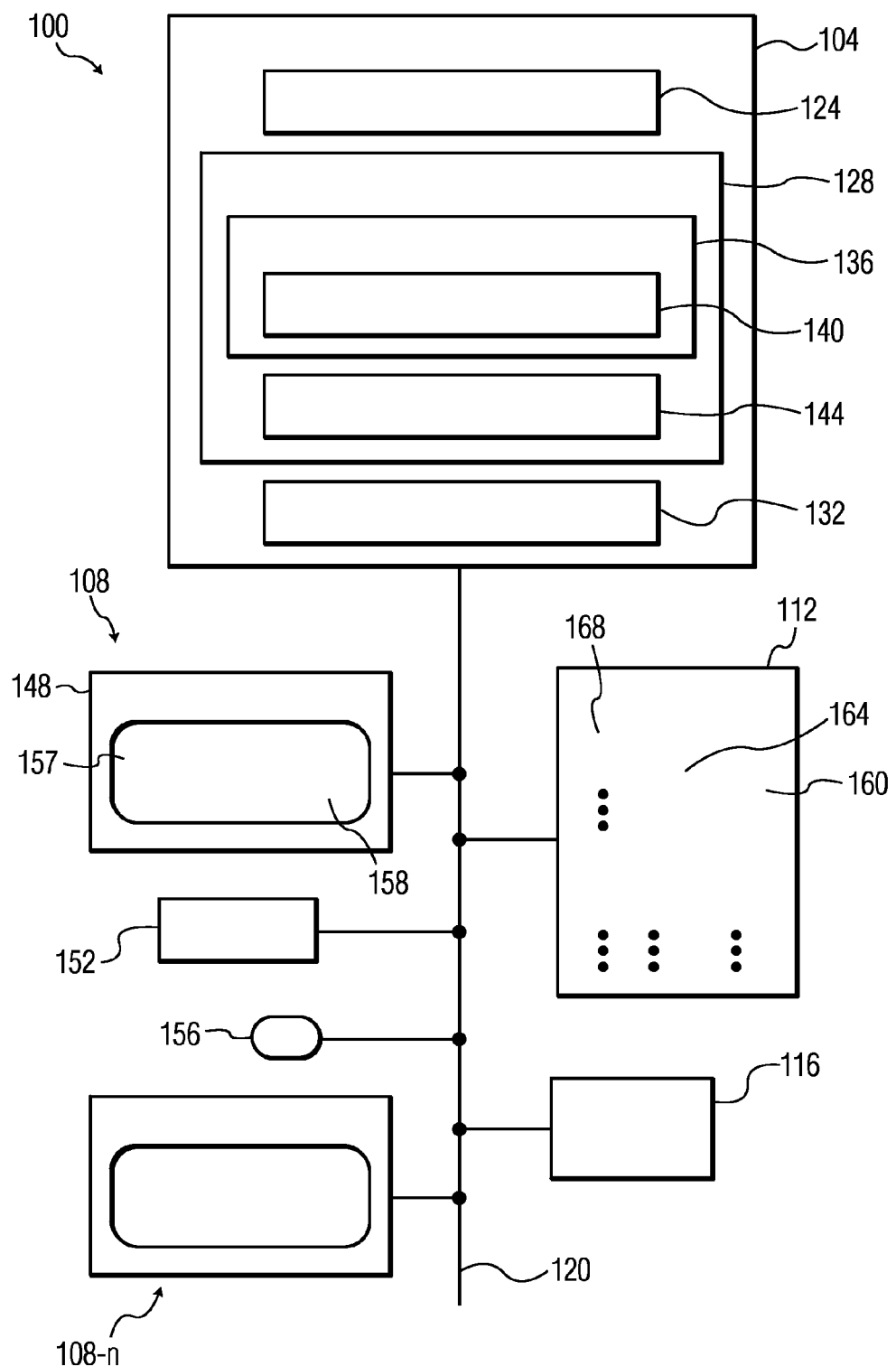
FIG. 1 is a block diagram of an exemplary context-aware decision-support system according to the present invention.

FIG. 1 depicts, by way of illustrative and non-limitative example, a context-aware decision-support system 100 according to the present invention. The system 100 includes a processor 104, user interfaces 108-1, 108-*n*, an electronic medical record (EMR) 112 and a storage memory 116, all mutually connected on a bus 120. The present invention, although principally directed to medical care, can be applied to decision support in administering legal advice, in automotive or computer network troubleshooting, and in other fields.

The processor 104 has a preparation module 124, a matching module 128 and a recommending module 132. The matching module 128 further includes a record search module 136 containing an identifier deriving module 140, and a guideline search module 144. Each of the modules may be implemented in hardware, software, firmware, or any combination of these.

The user interfaces 108-1, 108-*n* may be identical or differ, and the intervening dots represent any number of additional, identical or differing user interfaces. One of the interfaces 108-1, 108-*n* would typically be located at the hospital bed of an in-patient, and any of the other interfaces might be located at other beds, or at a central monitoring station. The interface 108-1 features a display screen 148, a keyboard 152 and a mouse 156. The display screen 148 may be a touch screen, and different or additional user-actuatable input devices, such as a track ball, light pen or any other known and suitable means, wired or wireless, may make up the user interface 108-1. Illustratively, the screen 148 displays a recommendation 157 to extubate, and a grade 158 "B" that indicates the level of evidence underlying the recommendation. The screen 148 is one means for presenting information to the clinician, although the means may include aural aspects, holographic display or other techniques.

The EMR 112 will typically store patient and clinical data of the hospital or institution. The hospital usually has one or more readily available coding schemes to represent information in its EMR 112, or to generate reports from the EMR for documentation and/or billing purposes. A number of coding systems in common use in hospitals include: CPT, ICD-9, ICD-10, DRG, LOINC, UMLS and SNOMED. The EMR 112 of the hospital may be modified to include identifiers or codes, for diseases, medical orders, medical procedures performed and medical diagnoses made, representative of steps of clinical guidelines encompassed by the context-aware decision-support system 100. A time or time stamp 160 is associated with each code 164 inserted into the EMR 112 in connection with the medical care of a patient 168. The time stamp 160 is ascertainable from the hospital's EMR 112 as is, or the EMR can be modified to include it. As seen in FIG. 1, the EMR 112 includes entries for all patients 168 and the codes 164 that apply to them.

The storage memory 116 preferably includes permanent or non-volatile storage, as well as temporary or working storage. The latter typically would include random access memory (RAM). Permanent storage can take the form of read-only memory (ROM) of flash memory. Any variation of the above memory devices can be utilized.

The clinical guidelines or "care processes" can also be referred to, among other characterizations, as treatment algorithms, critical pathways, protocols, standing orders or standard operating procedures. The steps of a clinical guideline typically involve, in at least some of the steps, branching to one of a plurality of possible next steps. The branch taken depends upon the outcome of a decision at the current step. The clinical guideline often has loops which are exited only at the point in medical treatment at which a different decision is made.

Examples of evidence grading systems include those designed by the American College of Cardiology (ACC), the Institute for Clinical Systems Improvement (ICSI), and the American College of Radiology (ACR). These grading systems differentiate between recommendations that are based on the highest level of evidence, such as randomized, controlled trial, and the lowest level of evidence, medical opinion. By indicating the level of evidence for important steps in the guideline or protocol, the clinician can confidently decide whether his/her patient fits the criteria for the specific decision.

A clinical guideline for Stable Coronary Artery Disease furnished by the ICSI, for example, numbers each box of a flow chart, so that each box can be regarded as a step in a predetermined multi-step service guideline. For each box, ICSI provides an algorithm annotation in the form of a plain language recommendation, followed by one or more level-of-evidence grades. The latter may exist as part of a trailing statement such as "Evidence supporting this recommendation is of class: R." "Class R" can denote a report that synthesizes or reflects upon collections of primary reports, and which has been subject to narrative review rather than systematic review. Accordingly, the Class R evidence is not the primary report on new data collection, and has not been through the most stringent peer review. The class grade pertains to research reports. ICSI also includes, with the guideline, conclusion grades for specific medical conclusions. These, too, may serve as level-of-evidence grades in the system 100.

Figure 2:
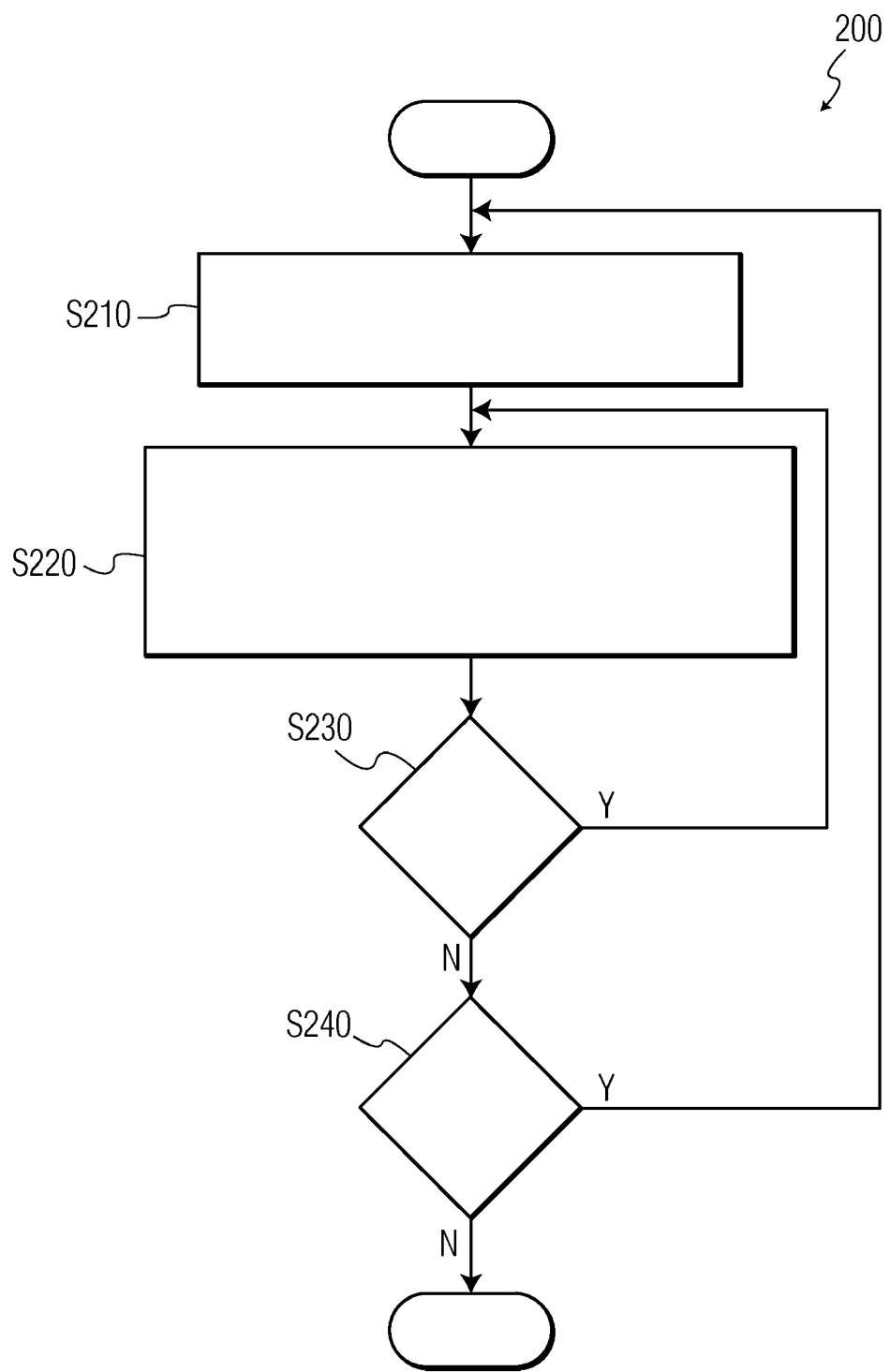
FIG. 2 is flow chart of a preparation process for the system of FIG. 1.

FIG. 2 shows an exemplary process 200 executable by the preparation module 124 to prepare the context-aware decision-support system 100 for further operation according to the present invention. Each clinical guideline to be tracked by the system 100 in furnishing decision support is stored in the storage memory 116 as an electronic representation (step S210). For preferably each step in the clinical guideline, a particular or unique hospital code is selected. As mentioned above, this may involve augmentation or modification of codes already in place in the EMR of the institution. The selected code is embedded in the electronic representation of the guideline, such as by inserting a literal in computer code, so that the code is logically linked to its particular, associated step in the guideline (step S220). The above procedure is carried out step-by-step for each guideline (steps S230, S240).

Before or after the preparation process 200, codes 164 and time stamps 160 are accumulated in the EMR 112 for patients 168 in the course of medical care provided by the hospital.

Figure 3:
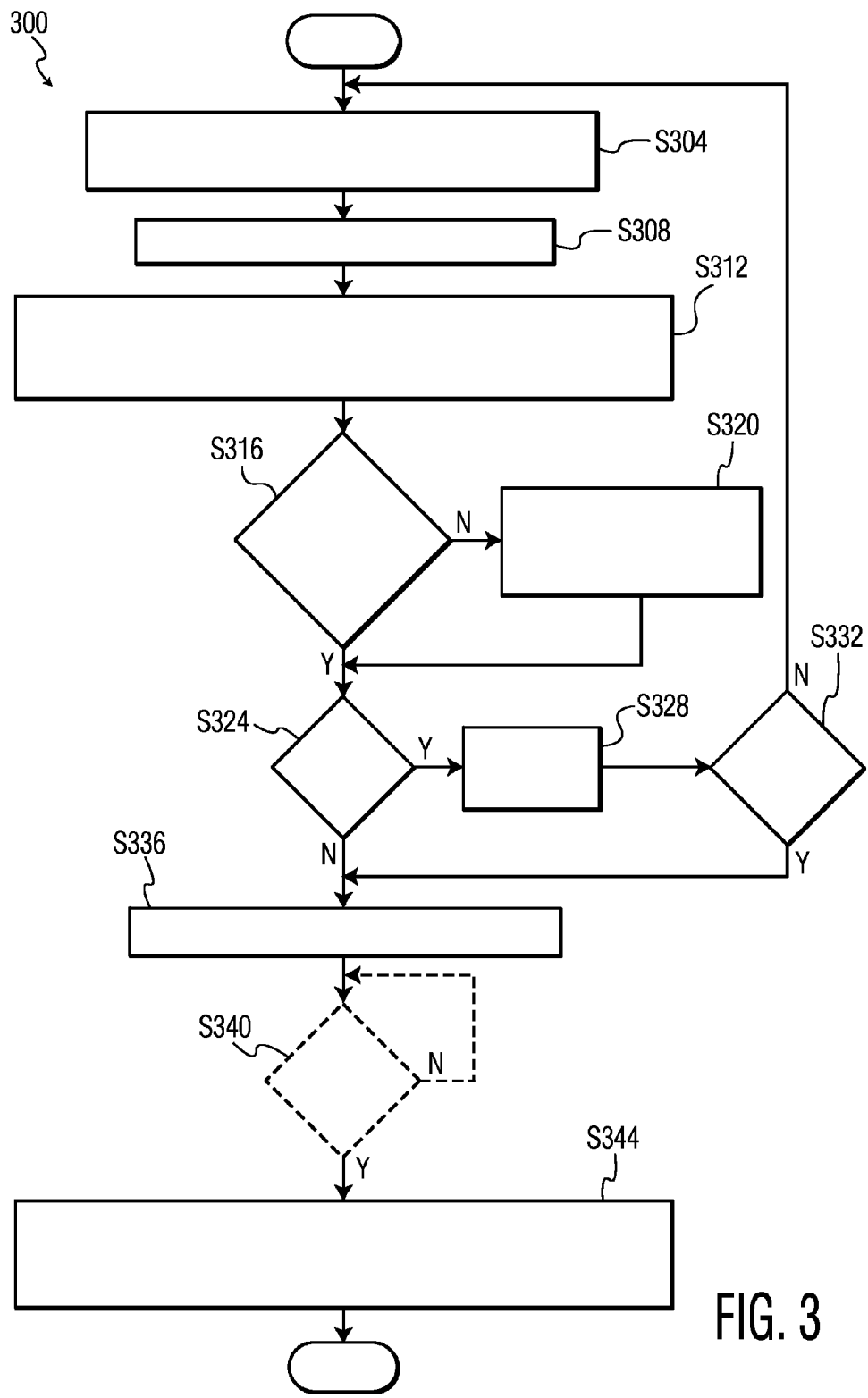
FIG. 3 is a flow chart showing operation of the system of FIG. 1.

FIG. 3 illustrates a possible embodiment for operating the system 100 in accordance with the present invention. First, the user may enter the name or other identification of the patient or subject 168 to bring up a screen on the display 148. The screen, presenting a recommendation 157 and grade 158, may be brought up without any further input or intervention by the user, according to an operating process 300 to be described below in connection with FIG. 3. In the event, however, the process 300 is already operating to furnish decision support for the patient 168, any addition, or particular types of additions, to the EMR 112 can automatically refresh the screen to reflect the newly added information.

Whether decision support is being initiated or updated for the patient at this point in time (step S304), identifier deriving module 140 searches the EMR 112 for hospital codes, pre-existing or newly added, that are linked or connected to the patient 168 (step S308). The found codes are collectively matched to a clinical guideline representation stored in step S220 (step S312).

In the simplest case, the found codes match codes linked in step S220 to a single stored guideline as the guideline the patient 168 is on or should be on. Even in this case, however, the time stamps 160 of the found codes may not match the temporal order of corresponding steps in the candidate guideline. Thus, temporal considerations are preferred to avoid the possibility of a mismatch. In addition, if the guideline repeats a particular step further down in the guideline, the logical temporal order of steps gleanable from guideline determines which of the two steps having duplicate codes matches a code found in the EMR 112. The matching module 128 can accordingly deduce the current step or stage or medical care.

More generally, however, a number of stored guidelines may each have one or more steps whose codes match the codes found in the EMR 112. In this case, the guideline search module 144 attempts to resolve the ambiguity as to the current guideline. Some codes may carry more weight than others in this regard, according to priority. Thus, a found code representing a particular diagnosis may strongly be linked to one or two guidelines, thereby narrowing the field of ambiguity or resolving the ambiguity. Temporal considerations may be utilized alternatively or in addition, based on the time stamps 160 associated with the found codes 164. For example, the temporal order of codes 164 found for a particular patient 168 may or may not be consistent with the corresponding temporal order of steps in a candidate guideline. In fact, two codes found for the patient 168 may be identical, i.e., duplicates, potentially corresponding to a loop in a guideline. Thus, their time stamps 160 distinguish between them, and the existence or non-existence of other codes of intervening temporality, representing intervening steps in the loop, could determine whether a candidate guideline is a match.

Optionally, the matching module 128 may use the location of the user interface 108-1 as a factor in determining the current guideline and/or current stage of medical care. The devices 148, 152, 156 may, for example, be commonly interfaced to the processor through a unique workstation connection that can be matched to physical location of the workstation by means of a look-up table in the storage memory 116. Thus, if the user interface 108-1 being operated in connection with the identified patient is located in the intensive care unit (ICU), the implied severity of a condition may be inferred in determining where the patient currently is in the guideline. As another example, if the user interface 108-1 being operated is located in the office of a particular cardiology specialist, this might imply a cardiac-related guideline and possibly a current stage of care in the guideline beyond the stage of being referred to the specialist.

In certain circumstances, the above measures for resolving the ambiguity may not suffice (step S316). The patient 168 may, for example, currently be under treatment at the hospital, in an in- or out-patient status, for two different ailments addressed by two respectively different guidelines. The processor 104 will, in such an event, send an on-screen query to the clinician. The query may ask which of the listed possible guidelines pertains to the current decision support. The clinician can, by means of the user interface 108-1, answer the query by selecting the current guideline (step S320). Another possibility is the appearance of a number of intervening missed steps in a guideline. The system 100 is preferably designed to issue a query whenever the system cannot definitively resolve an ambiguity as to the present guideline being followed.

On the other hand, the matching of the found hospital codes 164 to the steps of a candidate guideline can select a particular guideline, and even the current stage, in light of recognition that merely a single step has been missed between matched steps (step S324). The clinician is notified (step S328). If the clinician takes corrective action (step S332), the EMR 112 is updated by an addition in step S304; otherwise, the clinician may override the missed step (step S332).

Based on the steps matched, the matching module 144 automatically deduces the current stage (step S336).

Optionally, the clinician may solicit a recommendation on the next step in medical care (step S340); however, display of the recommendation is preferably automatically performed, without user intervention, based on addition or entry in step S304. The recommendation 157 is generally not merely a recitation of the next step in the guideline. Instead, the recommending module 132 utilizes information specific to the patient or subject 168, usually obtainable from the EMR 112, in making its recommendation 157. This information may be the present condition of the patient 168 or an assessment, fetched or derived, that the patient is high risk with respect to the ailment to which the guideline is directed. In traversing the guideline step-by-step, the recommending module 104 may skip, or supplement, a step accordingly. The recommendation may consist of phrases, sentences and paragraphs, amounting to a plain language statement of the recommended next step in treatment. The level-of-evidence grade 158 is also displayed (step S344). The items 157, 158 displayed are preferably hyperlinked for easy access to more detailed information. The display may include a list of order sets for the clinician to complete, since ascertainment of the current stage of medical care allows for this. The system 100 may execute the orders on demand, by contacting the appropriate departments if possible, or may print the desired orders for easy distribution. The display may appear on one, any or all the user interfaces 108-1, . . . , 108-n.

As has been demonstrated above, a context-aware decision support system according to the present invention, which dynamically selects the current guideline and dynamically tracks progress there through, enhances the speed to diagnosis and treatment, efficiently and cost-effectively. The system can quickly bring a medical provider up-to-date, and bridges the time-delay between clinical decisions such as ordering a test and using the test results to select the next step. The system, moreover, facilitates immediate assessment by the clinician of recommendations which are tailored to patient-specific information.

The invention claimed is:

1. A context-aware decision support device comprising:
   a user interface; and
   a decision support initialization device configured to search through an electronic record of service for identifiers to enable automatic deduction of a current stage of service in a predetermined multi-step service guideline, to thereby enable making of a decision based on the deduced current stage, and is configured for detecting, from said record, that a step in said guideline has been missed, and for reporting, by means of said interface, detection of the missed step.

2. The decision support device of claim 1, wherein said identifiers are codes pre-assigned to respective diseases, medical orders, medical procedures and medical diagnoses.

3. The decision support device of claim 1, further configured for, before the searching, linking said identifiers to steps in electronic representations of respective candidate predetermined multi-step service guidelines one of which is said guideline.

4. The decision support device of claim 1, wherein the searching and deducing are performed for a particular service recipient in said record.

5. The decision support device of claim 4, wherein said searching is event-driven by addition to said record for said recipient.

6. The decision support device of claim 1, wherein said record is an electronic medical record and said service is medical care.

7. The decision support device of claim 1, wherein the a user interface recommends, based on the deduced current stage and information specific to said recipient, a next step in serving said recipient.

8. The decision support device of claim 1, configured for, in performing the deducing, selecting said guideline, automatically and without user intervention, for a given service recipient, and from among a plurality of candidate predetermined multi-step service guidelines.

9. A context-aware decision support apparatus, comprising:
   a module for automatically deducing a current stage of service, wherein the module for deducing is configured for matching a predetermined multi-step service guideline against an electronic record of service to thereby automatically deduce, from said record with respect to a service recipient in said record, said current stage in said guideline, wherein the module for automatically deducing comprises:
      an identifier deriving module configured for deriving, front said record, ones of the particular identifiers connected to said service recipient; and
      a guideline search module configured for searching the linked representations for a collective match of the derived ones of the identifiers to a representation of said representations, wherein said record links respective times to said identifiers associated with the service recipient, said matching module being further configured for detecting at least one of duplicates from among said derived ones of the identifiers and duplicates from among the identifiers linked to said respective steps, for fetching said respective times for the detected duplicates, and for performing said matching based on the fetched times;

a preparation module configured for making representations of predetermined multi-step service guidelines, said guideline being one of said guidelines, and linking, in corresponding ones of said representations, identifiers to respective steps of said guidelines;

a user interface; and a recommending module to be activated for automatically, and without user intervention:
   a) retrieving a predetermined grade symbolizing level of confidence in evidence underlying a recommendation that is based on the deduced current stage; and
   b) presenting said recommendation and the retrieved grade on said user interface.

10. The apparatus of claim 9, wherein said recommending module is activated automatically, and in response to the deducing.

11. The apparatus of claim 9, wherein said record is an electronic medical record; said service is medical care, and said service recipient is a patient or medical subject.

12. The apparatus of claim 9, wherein the module for deducing comprises a guideline search module for searching through a representation of said guideline, to detect a step in said guideline indicative of said current stage of service.

13. The apparatus of claim 9, wherein said module for deducing comprises:
   a record search module that is event-driven by additions to said record; and
   a guideline search module for comparing between said guideline and output of said record search module to detect a match in said matching.

14. A computer implemented method for decision support, comprising:
   connecting, in a record, a service recipient to one or more hospital codes;
   entering an identifier of the service recipient;
   automatically deducing a current stage of service by matching a predetermined multi-step service guideline against said record to automatically deduce, from said record with respect to the service recipient in said record, a current stage of service in said guideline, wherein said matching is based on the entered identifier and performed without need for further entry of information; and,
   automatically or in response to user request:
      a) retrieving, automatically and without user intervention, a grade symbolizing level of confidence in evidence underlying a recommendation that is based on the deduced current stage; and
      b) presenting, automatically and without user intervention, said recommendation and the retrieved grade.

15. The method of claim 14, wherein said retrieving and said presenting are operable to occur automatically in response to the deducing.

16. A computer program product comprising a computer readable medium in which is embedded a program that includes instructions executable by a processor to perform the method of claim 14.

17. A decision support initialization device comprising:
   a plurality of separately-located user interfaces, and
   a processor configured to search through an electronic record of service to enable, based on said search and a location of an interface of said interfaces that is operated, automatic deduction of a current stage of service in a predetermined multi-step guideline, to thereby enable making of a decision based on the deduced current stage, wherein the processor is further configured for detecting, from said record, that a step in said guideline has been missed, and for reporting, by means of said interface, detection of the missed step.

* * * * *